United States Patent [19]

Refojo et al.

[11] Patent Number: 5,336,487

[45] Date of Patent: Aug. 9, 1994

[54] METHOD OF TREATING EYE DISORDERS WITH SILICON/FLUOROSILICONE COPOLYMER OIL

[76] Inventors: Miguel F. Refojo, 2 Lowell Rd., Wellesley, Mass. 02181; Felipe I. Tolentino, 9 Hawthorne Pl., Unit 16E, Boston, Mass. 02114

[21] Appl. No.: 27,253

[22] Filed: Mar. 5, 1993

[51] Int. Cl.$^5$ .................. A61K 31/74; A61K 31/695
[52] U.S. Cl. .................. 424/78.04; 514/63; 514/912
[58] Field of Search ............ 514/772, 63, 912; 424/78.04

[56] References Cited

U.S. PATENT DOCUMENTS 4,490,351 12/1984 Clark, Jr. .

OTHER PUBLICATIONS

*Silicone Oil in the Treatment of Complicated Retinal Detachments*, K. Lucke and H. Laqua, Springer-Verlag, N.Y., 1990, pp. 8–15, 124, 125.
"Experimental Studies of the Combined Use of Vitreous Substitutes of High and Low Specific Gravity", Sparrow et al., *Retina*, 12:134–140, (1992).
"Long-Term Vitreous Replacement in Primates with Intravitreal Vitreon or Vitreon Plus Silicone", Peyman et al., *Ophthalmic Surgery*, V. 122, No. 11, pp. 657–664 (Nov. 1991).
"Vitreous Injections: When to do Them and Why", Tolentino et al., *Ophthalmology Annual*, 1989, Raven Press, N.Y., pp. 337–349.
"Ciliary Sulcus Fixation of a Dislocated Posterior Chamber Intraocular Lens Using Liquid Perfluorophenanthrene", Fanous et al., *Ophthalmic Surgery*, V. 23, No. 8, pp. 551–552 (Aug. 1992).
"Perfluorocarbon Liquids in the Management of Traumatic Retinal Detachments", Chang et al., *Opthalmology*, vol. 96, No. 6, pp. 785–792 (Jun. 1989).
"Low Viscosity Liquid Fluorochemicals in Vitreous Surgery", Chang, *American Journal of Ophthalmology*, 103:38–43, (Jan. 1987).
*Proliferative Vitreoretinopathy*, H. Freeman and F. Tolentino, Eds., Springer-Verlag, N.Y., 1988, pp. 162–165.
"Factors Contributing to the Emulsification of Intraocular Silicone and Fluorosilicone Oils", Nakamura et al., *Investigative Ophthalmology and Visual Science* V. 31, No. 4, pp. 647–656 (Apr. 1990).
"Analysis and Fractionation of Silicone and Fluorosilicone Oils for Intraocular Use", Nakamura et al., *Investigative Ophthalmology and Visual Science*, V. 31, No. 10, pp. 2059–2069 (Oct. 1990).
"Fluorinated Oils as Experimental Vitreous Substitutes", Miyamoto et al., *Archives of Ophthalmology*, vol. 104, p. 1053–1056 (Jul. 1986).
"Perfluorooctane in the Treatment of Giant Retinal Tears with Proliferative Vitreoretinopathy", Glaser et al., *Ophthalmology*, vol. 98, No. 11, pp. 1613–1621 (Nov. 1991).
"Management of the Dislocated Crystalline Lens with a Perfluorocarbon Liquid", Shapiro et al., *American Journal of Ophthalmology*, 112:401–405 (Oct. 1991).
"Ocular Toxicity of Low Molecular-Weight Components of Silicone and Fluorosilicone Oils", Nakamura et al., *Investigative Ophthalmology and Visual Science* vol. 32, No. 12, pp. 3007–3020 (Nov. 1991).
Brochure entitled "Vitreon", Vitrophage, Inc., Lyons, Ill. (1984).

*Primary Examiner*—Zohreh Fay
*Attorney, Agent, or Firm*—Brian M. Dingman

[57] ABSTRACT

A method of treating an intraocular structural disorder of an eye comprising introducing into the intraocular structure under treatment a liquid silicone/fluorosilicone oil in an amount effective to treat the intraocular structural disorder.

21 Claims, No Drawings

METHOD OF TREATING EYE DISORDERS WITH SILICON/FLUOROSILICONE COPOLYMER OIL

GOVERNMENT RIGHTS

This invention was made under NIH Grant RO-1EY00327. The government has certain rights in this invention.

FIELD OF INVENTION

This invention relates to methods of treating eye disorders with a liquid silicone/fluorosilicone copolymer oil that has a relatively low tendency toward intraocular emulsification and a specific gravity just greater than water so that it is effective to push back and maintain in place an inferior detached retina.

BACKGROUND OF INVENTION

There have been proposed and used a number of gases and liquids for treating eye disorders. Liquids that have been used as intraocular tools include silicone oils (polydimethysiloxanes), fluorosilicone oils such as polymethyl-3,3,3-trifluoropropylsiloxane and a number of perfluorocarbon liquids, for example perfluorooctane, perfluorodecalin and perfluorophenanthrene (perfluorotetradecahydrophenanthrene).

One use of these liquids is in vitreoretinal surgery. The properties of the liquid for such use should be that it is transparent with a refractive index close to that of the vitreous. The substance should not mix with the vitreous, nor should it disperse or emulsify in the vitreous. Of course it should also be chemically and physiologically inert. To effectively act as a retinal tamponade, the substance should have a high interfacial tension and a high surface tension.

Silicone oils have been used for a number of years in vitreoretinal surgery. They are also known to be used for treating other disorders of the eye as set forth in U.S. Pat. No. 4,490,351, incorporated herein by reference. Silicone oil is transparent with a refractive index of 1.404 (the refractive index of water is 1.33), and a specific gravity of 0.97. It has a relatively high interfacial and surface tension, making it useful as a retinal tamponade. However, because the specific gravity of silicone oil is less than that of water, it is not useful as a tamponade for an inferior detached retina. Further, the viscosity of the silicone oils commonly used in vitreoretinal surgery is from 1,000 to 12,000 cs. The high viscosity makes it relatively difficult to handle, requiring the surgeon to use a silicone oil pump to pump the liquid through the needle in to and out of the eye.

Fluorosilicone oil has a higher specific gravity of 1.29 and also has a relatively high surface and interfacial tension. The fluorosilicone oils in experimental use have a viscosity in the same range as the silicone oil. Accordingly, they are just as difficult to work with. An additional problem with the fluorosilicone oils, however, is its tendency to emulsify in the eye. It appears that the dispersion of the fluorinated oil is stabilized in the eye by surface active proteins that interact with the highly electronegative fluorine atoms pendant on the polysiloxane backbone. Accordingly, fluorosilicone oils do not appear to be useful as long-term vitreous replacements for vitreoretinal surgery.

A number of perfluorocarbon liquids have also been investigated for treating eye disorders, particularly for intravitreous surgery. The relatively high specific gravity of about 2 makes them useful as an inferior detached retina tamponade. The high density could however damage the sensitive retinal tissue. In addition, the viscosity of the fluorocarbon liquids is only from about 1 to 8 cs, leading to more potential for emulsification in the vitreous. Further, the extremely high specific gravity also increases the chances of dispersion of the liquid in the vitreous. This dispersion, or "fish egging", of the perfluorocarbon liquids is more pronounced because of the number of fluorine atoms present in the compound that act to stabilize the dispersed liquid droplets. Accordingly, these liquids must be replaced in a second surgical procedure soon after the first repair procedure.

The use of silicone oil and perfluorocarbon liquids together has also been studied. See, for example, *Ophthalmic Surgery* "Long-Term Vitreous Replacement in Primates with Intravitreal Vitreon or Vitreon Plus Silicon", G. A. Peyman et al., V. 22, No. 11, November 1991, pages 657–664; *Retina* "Experimental Studies of the Combined Use of Vitreous Substitutes of High and Low Specific Gravity", J. R. Sparrow et al., V. 12, No. 2, 1992, pages 134–140. The silicone oil is useful as a tamponade for superior retinal detachments, and the perfluorocarbon for inferior retinal detachments. The use of the two together provides tamponade and mechanical support of both portions of the retina simultaneously. However, since the liquids are immiscible, the volumes of each must be carefully controlled for effective use. In addition, the great viscosity and density differences between the liquids leads to a greater tendency toward dispersion, which is offset to some extent by the lower fluorine concentration as compared to pure perfluorocarbon liquid (but not as compared to pure silicone oil). Because perfluorocarbons are used, however, this procedure requires that the tamponade be relatively quickly removed and replaced in a second surgical procedure.

SUMMARY OF INVENTION

It is therefore an object of this invention to provide a substance that is well suited for treating various eye disorders.

It is a further object of this invention to provide methods of treating eye disorders with a liquid silicone/fluorosilicone copolymer oil.

It is a further object of this invention to provide a vitreoretinal surgery method employing a substance that has a specific gravity just greater than the vitreous so that it may be used to push back and maintain in place an inferior detached retina without damaging the retina.

It is a further object of this invention to provide such a method employing an oil that can be used to manipulate the retina and can be left in the eye for sufficient time to allow healing of the retina before removal.

It is a further object of this invention to provide such a method employing an oil of relatively low viscosity.

It is a further object of this invention to provide such a method employing an oil with a relatively low tendency to emulsify in the vitreous.

It is a further object of this invention to provide such a method employing an oil which has a lower tendency to disperse in the vitreous.

It is a further object of this invention to provide such a method employing an oil which has less fluorine than fluorosilicone oils and perfluorocarbon liquids.

It is a further object of this invention to provide such a method employing an oil that is relatively easy for the surgeon to inject and remove from the eye.

It is a further object of this invention to provide such an oil that can act on both the anterior and posterior retina at the same time.

It is a further object of this invention to provide such an oil that can do away with the first removal procedure required with other compounds.

It is a further object of this invention to provide such an oil that can also deliver an anti-proliferative agent.

This invention results from the realization that eye disorders, particularly detached and/or torn retinas, can be effectively treated employing a purified silicone/fluorosilicone copolymer oil that is just heavier than water, has a refractive index close to that of the vitreous, has a relatively low viscosity, and a relatively high surface tension and interfacial tension so that it is an effective tamponade for an inferior detached retina.

This invention features methods of treating intraocular structural disorders of an eye. In one embodiment the method includes introducing into the intraocular structure under treatment a liquid copolymer of silicone oil and fluorosilicone oil (silicone/fluorosilicone copolymer oil) in an amount effective to treat the intraocular structure disorder. In a preferred embodiment, the copolymer includes nominally approximately 50% of each monomer. The copolymer is preferably purified before introduction into the intraocular structure, for example by removing lower molecular weight impurities in the copolymer.

The copolymer may be introduced into the vitreous, the aqueous, and/or the lens, The copolymer is particularly well suited as a vitreous replacement retinal tamponade for vitreoretinal surgery.

The copolymer preferably has a viscosity of 175 to 200 cs, a specific gravity of approximately 1.15, and a refractive index of approximately 1.38. In one use, the copolymer has dissolved in it before introduction into the intraocular structure an anti-proliferative agent such as retinoic acid.

Also featured is a method of repairing a retinal disorder of an eye comprising locating the eye so that the choroid is under the retina, and introducing into the vitreous cavity of the eye a liquid copolymer of silicone oil and fluorosilicone oil to maintain the retina against the choroid. The retinal disorder may be a detached and/or a torn retina. Preferably, the copolymer includes nominally approximately 50% of each monomer, has a viscosity of approximately 175 to 200 cs, a specific gravity of approximately 1.15, and a refractive index of approximately 1.38. The copolymer is stable and tolerated sufficiently so that it may be left in the eye for sufficient time for healing to begin, up to eight to ten weeks or longer.

Also featured is a method of simultaneously repairing an anterior and posterior detached or torn retina comprising replacing at least a portion of the vitreous of the eye with a liquid copolymer of silicone oil and fluorosilicone oil to maintain both the anterior and posterior retina against the choroid.

This invention also features a method separating adjacent tissue layers comprising introducing between the tissue layers a liquid copolymer of silicone oil and fluorosilicone oil in an amount sufficient to separate adjacent tissue layers.

DISCLOSURE OF PREFERRED EMBODIMENTS

Other objects, features and advantages will occur to those skilled in the art from the following description of preferred embodiments.

This invention may be accomplished in methods of treating eye disorders employing a liquid silicone/fluorosilicone copolymer oil.

The term "silicone oil" as used herein means polydimethylsiloxane having the following formula:

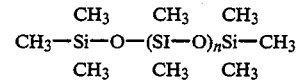

The term "fluorosilicone oil" as used herein means polymethyl-3,3,3-trifluoropropylsiloxane having the following formula:

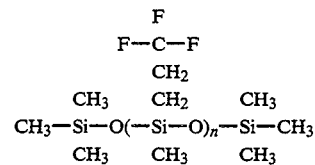

The term "perfluorocarbon liquids" as used herein means the compounds disclosed in U.S. Pat. No. 4,490,351.

The term "silicone/fluorosilicone copolymer oil", and "copolymer of silicone oil and fluorosilicone oil", as used herein means polymethyl-3,3,3-trifluoropropylsiloxanedimethylsiloxane copolymer having the following formula:

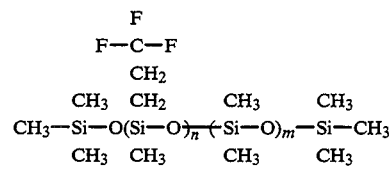

where n and m may or may not be approximately equal.

The silicone/fluorosilicone copolymer oil used in the methods of this invention is made by copolymerizing the monomers of silicone oil and fluorosilicone oil. The result is an oil with the properties listed in Table I as compared to silicone oil and fluorosilicone oil.

TABLE I

| | Silicone/Fluorosilicone Oil | Silicone Oil | Fluorosilicone Oil |
|---|---|---|---|
| Viscosity, cs | 175–200 | 1,000–12,000 | 1,000–10,000 |
| Refractive Index, (@25° C.)$n_o$ | 1.38 | 1.404 | 1.382 |
| Density g/cm$^3$ | 1.15 | 0.97 | 1.29 |
| Surface tension, (@37° C.) dyne/cm | 22 | 20 | 23 |
| Interfacial tension, (@37° C.) dyne/cm | 41 | 44 | 39 |

Silicone/fluorosilicone copolymer oil thus has a relatively low viscosity making it relatively easy to inject and remove from the eye. The viscosity may be adjusted up or down by altering the length of the polymer chains. Additionally, silicone/fluorosilicone copolymer oil has a specific gravity of only 1.15 which allows it to be used to push back and maintain in place an inferior detached retina without being so dense that it could damage the retina, thus allowing the copolymer oil to be left in the eye for a longer time than the perfluorocarbon liquids.

The silicone/fluorosilicone copolymer oil also has a relatively high surface and interfacial tension making it well suited for manipulation of the retina while decreasing the likelihood of dispersion and emulsification. Additionally, silicone/fluorosilicone copolymer oil has only a fraction of the fluorine found in the fluorosilicone oils and the perfluorocarbon liquids. Accordingly, the silicone/fluorosilicone copolymer oil does not disperse in the vitreous as readily as the more fluorinated compounds, the perfluorocarbons.

Another advantage of the silicone/fluorosilicone copolymer oil as opposed to the perfluorocarbon liquids, particularly perfluorophenanthrene, is that the refractive index is sufficiently different from that of the liquefied vitreous so that the physician may distinguish between the two in the eye.

Crude silicone/fluorosilicone copolymer oil is available from Huls Petrarch Systems in Bristol, Pa., as polymethyl-3,3,3-trifluoropropylsiloxane-50% dimethylsiloxane copolymer. When this crude compound was analyzed by gas chromatography as previously reported for silicone and fluorosilicone oil in *Inv. Opthalmol. & Vis. Sci.*, 31: 2059-2069, 1990, Nakamura K., Refojo, M. F., Crabtree, D. V., and Leong, F. L.: Analysis and Fractionation of Silicone and Fluorosilicone Oils for Intraocular Use, a relatively large amount of low molecular weight components were detected. Since these low molecular weight components are not tolerated by the tissue of the eye, the higher molecular weight polymer was separated from those lower molecular weight components by fractionation using the extraction technique reported in the subject reference. The oil was extracted with 95% ethyl alcohol for six weeks to remove the low molecular weight components. Then, a rotating evaporator was used to remove the alcohol dissolved in the high molecular weight fraction of the silicone/fluorosilicone copolymer oil. Any residual alcohol and low molecular weight components still remaining in the silicone/fluorosilicone copolymer oil were then removed by distillation under high vacuum. The silicone/fluorosilicone copolymer oil was then treated with activated charcoal and filtered twice through filter paper (Whatman No. 114). Finally, the purified silicone/fluorosilicone copolymer oil was filtered again through a 0.2 micron filter unit available from Millipore Company. The fractionation procedure yielded about 60% of the crude silicone/fluorosilicone copolymer oil. No alcoholysis was observed in the silicone/fluorosilicone copolymer oil. The resulting product was not soluble in silicone oil or fluorosilicone oil, indicating that it is indeed a different chemical compound.

The methods of this invention are not limited to a silicone/fluorosilicone copolymer oil having 50% of each monomer. As the proportion of the fluorosilicone monomer is increased, the specific gravity of the silicone/fluorosilicone copolymer oil will increase, but the increased number of fluorine atoms will lead to a greater tendency toward emulsification. In contrast, as the silicone oil monomer portion is increased above 50%, the specific gravity will decrease and there will be a lesser tendency to emulsification.

EXAMPLE I

Because of the high specific gravity and viscous property of the silicone/fluorosilicone co-polymer, it can be used as a mechanical tool to flatten and re-attach large retinal tears of the human eye involving more than a quadrant of the retina. These tears called Giant Tears have unfavorable prognosis because their posterior component tends to curl up. The procedure consists of (1) removal of the vitreous gel by vitrectomy (excision and removal by means of a vitrector) through the pars plana of the eye through the microscope, (2) injection of the co-polymer in the vitreous near the surface of the retina but posterior to the curled retina, until the polymer unfurls the retina and fills up the vitreous cavity, and (3) application of intraocular laser along the margins of the retinal tear. It takes four to six weeks for the laser treatment to completely seal and heal the retinal tear and subsequent removal of the co-polymer from the eye.

EXAMPLE II

By hydraulic forces the co-polymer can be used to delaminate a sheet of abnormally formed tissue membrane on the retinal surface by virtue of its weight and viscosity. This procedure is performed in the human eye in conjunction with vitrectomy for diabetic traction retinal membranes and permits the surgeon to remove retinal tissue membrane safely to flatten retinal folds. The separated tissue membrane is finally removed by vitrectomy. The co-polymer is removed from the eye after the procedure.

EXAMPLE III

Another use of the co-polymer is the removal of accidentally displaced intraocular lens implant or dislodged lens nuclear fragments in the human eye during phaco emulsification. Because of the high specific gravity of the co-polymer, the materials can be displaced in the front or in the anterior chamber of the eye where they can be repositioned and fixed with a suture in the case of an intraocular implant, or removal by phaco emulsification in the case of a nuclear fragment.

Silicone/fluorosilicone copolymer oil is thus useful in the same manner that the perfluorocarbon liquids, silicone oils and fluorosilicone oils are currently used for. The intraocular treatments that may be accomplished with silicone/fluorosilicone copolymer oil include replacement of some or all of the vitreous, typically accomplished concurrently with removal of the vitreous being replaced. Additionally, the liquid may be used to replace some or all of the aqueous. The liquid may also be introduced into the lens to form a substantially transparent window therein.

One major use of silicone/fluorosilicone copolymer oil is for vitreoretinal surgery, particularly as a tamponade for inferior and/or superior detached retinas. The compound may remain in the eye for at least the eight to ten weeks necessary for the healing process. Accordingly, detached and/or torn retinas may be repaired with a single operative procedure as opposed to the two procedures required when using perfluorocarbon liquids and other substances that may not remain in the eye for a sufficient time to allow healing to commence. In the procedure, the eye is positioned so that the choroid is under the retina, and the copolymer is introduced to push the retina back in place and hold it against the choroid. If the liquid level covers the detachment, the weight of the liquid will gently maintain the retina in place against the choroid until healing at least commences.

Silicone/fluorosilicone copolymer oil may also be used for other procedures accomplished with inert liquids. For example, hydraulic laminar separation or hydrodissection to separate tissue layers may be accomplished by injecting silicone/fluorosilicone copolymer oil between the tissue layers in an amount sufficient to separate the layers.

Anti-proliferative drugs such as the vitamin A derivative retinoic acid are used to prevent unwanted growth in the posterior chamber of the eye. However, only liposoluble drugs can be used in silicone oils, and no drug will dissolve in the perfluorocarbon liquids. It has been found that retinol and retinoic acid dissolve in silicone/fluorosilicone copolymer oil thus creating the possibility of delivering an anti-proliferative agent into The vitreous cavity along with the silicone/fluorosilicone copolymer oil not only as the tamponade agent but also as the vehicle for the delivery of the drug.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A method of manipulating the retina, holding the retina in place, displacing a dislocated lens, or delaminating tissue in the eye, comprising introducing into the eye a liquid silicone/fluorosilicone copolymer oil in an amount effective to accomplish the method.

2. The method of claim 1 further including the step of adding a drug or other substance to the liquid silicone/fluorosilicone copolymer oil before its introduction into the eye.

3. The method of claim 1 in which said copolymer includes nominally approximately 50% of each monomer.

4. The method of claim 1 in which said copolymer is purified before introduction into the intraocular structure.

5. The method of claim 4 in which the purification removes lower molecular weight impurities in the copolymer.

6. The method of claim 1 in which said copolymer is introduced into the vitreous of the eye.

7. The method of claim 1 in which said copolymer is introduced into the aqueous of the eye.

8. The method of claim 1 in which said anti-proliferative agent includes retinoic acid or retinol.

9. The method of claim 1 in which said copolymer is introduced into the lens of the eye.

10. The method of claim 1 in which said copolymer has a viscosity of approximately 175–200 cs.

11. The method of claim 1 in which said copolymer has a specific gravity of approximately 1.15.

12. The method of claim 1 in which said copolymer has a refractive index of approximately 1.38.

13. The method of claim 1 in which said copolymer has dissolved in it before introduction into the intraocular structure an anti-proliferative agent.

14. A method of manipulating a detached or torn retina comprising locating the eye so that the choroid is under the retina, and introducing into the vitreous cavity of the eye a liquid silicone/fluorosilicone copolymer oil in an amount sufficient to maintain the retina against the choroid.

15. The method of claim 14 in which said copolymer includes nominally approximately 50% of each monomer.

16. The method of claim 14 in which said copolymer has a viscosity of approximately 175–200 cs.

17. The method of claim 14 in which said copolymer has a specific gravity of approximately 1.15.

18. The method of claim 14 in which said copolymer has a refractive index of approximately 1.38.

19. The method of claim 14 in which said copolymer is left in the eye for sufficient time for healing to begin.

20. A method of simultaneously repairing an anterior and posterior detached or torn retina comprising replacing at least a portion of the vitreous of the eye with a liquid silicone/fluorosilicone copolymer oil in an amount sufficient to maintain the anterior and posterior retina against the choroid.

21. A method of separating adjacent tissue layers comprising introducing between said tissue layers a liquid silicone/fluorosilicone copolymer oil in an amount sufficient to separate said adjacent tissue layers.

* * * * *